United States Patent [19]
Fraser et al.

[11] Patent Number: 6,034,768
[45] Date of Patent: Mar. 7, 2000

[54] INDUCED BREAKDOWN SPECTROSCOPY DETECTOR SYSTEM WITH CONTROLLABLE DELAY TIME

[75] Inventors: Mark E. Fraser, Nashua, N.H.; Karl Holtzclaw, Richardson, Tex.; Amy Hunter, Andover, Mass.; Steven J. Davis, Londonderry, N.H.; Lawrence G. Piper, Reading, Mass.

[73] Assignee: Physical Sciences Inc., Andover, Mass.

[21] Appl. No.: 09/114,147

[22] Filed: Jul. 13, 1998

Related U.S. Application Data

[60] Provisional application No. 60/060,162, Sep. 26, 1997.

[51] Int. Cl.⁷ .............................. G01N 21/63; G01J 3/30
[52] U.S. Cl. ............................ 356/316; 356/317; 216/60
[58] Field of Search .................... 356/317, 318, 356/417, 418, 316, 314; 216/60

[56] References Cited

U.S. PATENT DOCUMENTS

| | | |
|---|---|---|
| 3,883,764 | 5/1975 | Johnson et al. . |
| 3,945,907 | 3/1976 | Gokhale . |
| 4,238,198 | 12/1980 | Swaim et al. . |
| 4,447,153 | 5/1984 | Cremers et al. . |
| 4,540,884 | 9/1985 | Stafford et al. . |
| 4,544,274 | 10/1985 | Cremers et al. . |
| 4,561,777 | 12/1985 | Radziemski et al. ............... 356/318 |
| 4,645,342 | 2/1987 | Tanimoto et al. .................. 345/318 |
| 4,725,422 | 2/1988 | Miyabayashi et al. . |
| 4,780,608 | 10/1988 | Cross et al. . |
| 4,801,209 | 1/1989 | Wadlow ............................. 356/316 |
| 4,846,920 | 7/1989 | Keller et al. ....................... 216/60 |
| 4,925,307 | 5/1990 | Cremers et al. .................... 356/318 |
| 4,993,834 | 2/1991 | Carlhoff et al. . |
| 4,995,723 | 2/1991 | Carlhoff et al. . |
| 5,085,499 | 2/1992 | Griffin et al. ...................... 356/316 |
| 5,245,406 | 9/1993 | Masutani . |
| 5,251,008 | 10/1993 | Masutani . |
| 5,252,834 | 10/1993 | Lin . |
| 5,290,383 | 3/1994 | Koshimizu ......................... 156/345 |
| 5,303,025 | 4/1994 | Fukui et al. . |
| 5,363,189 | 11/1994 | Fukui et al. . |
| 5,379,103 | 1/1995 | Zigler . |
| 5,446,538 | 8/1995 | Noll . |
| 5,469,255 | 11/1995 | Kamada et al. . |
| 5,537,207 | 7/1996 | Carlhoff et al. . |
| 5,583,634 | 12/1996 | Andre et al. . |
| 5,751,416 | 5/1998 | Singh et al. ....................... 356/318 |
| 5,781,289 | 7/1998 | Sabsabi et al. .................... 356/318 |

OTHER PUBLICATIONS

Nakamura, S. et al., "Determination Of An Iron Suspension In Water By Laser–Induced Breakdown Spectroscopy With Two Sequential Laser Pulses," *Analytical Chemistry*, vol. 68, No. 17, Sep. 1, 1996, pp. 2981–2986.

Piper, L.G. et al., "Portable Sensor For Hazardous Waste," *Physical Sciences Inc.*, Oct. 22–24, 1996.

Sattmann, R. et al., "Laser–Induced Breakdown Spectroscopy Of Steel Samples Using Multiple Q–Switch Nd:YAG Laser Pulses," *IOP Publishing Ltd.*, Jul. 14, 1995, pp. 2181–2187.

*Primary Examiner*—Frank G. Font
*Assistant Examiner*—Zandra V. Smith
*Attorney, Agent, or Firm*—Hunton & Williams

[57] ABSTRACT

The invention relates to high power, spark induced breakdown spectroscopy (SIBS) detectors with controllable delay time and to spark induced breakdown spectroscopy plasma generators with dual electrodes with specific electrode material, both for use in methods and apparatuses for detecting spectral signatures of atomic emissions, (e.g., from heavy metals such as lead, mercury, chromium, cadmium, arsenic, antimony and beryllium and radioactive materials such as uranium, plutonium, thorium and technetium) for measuring, for example, atomic concentrations of samples such as vapors and airborne particulates.

30 Claims, 4 Drawing Sheets

INDUCED BREAKDOWN SPECTROSCOPY DETECTOR SYSTEM WITH CONTROLLABLE DELAY TIME

This application claims benefit of Provisional Appl. 60/060,162 filed Sep. 26, 1997.

FIELD OF THE INVENTION

The invention relates to high power, spark induced breakdown spectroscopy (SIBS) detectors with controllable delay time and to spark induced breakdown spectroscopy plasma generators with dual electrodes with specific electrode material, both for use in methods and apparatuses for detecting spectral signatures of atomic emissions, (e.g., from heavy metals such as lead, mercury, chromium, cadmium, arsenic, antimony and beryllium and radioactive materials such as uranium, plutonium, thorium and technetium) for measuring, for example, atomic concentrations of samples such as vapors and airborne particulates.

BACKGROUND OF THE INVENTION

In general, SIBS techniques can be used to detect and quantitatively measure concentrations of elements in a given material of interest. These measurements can be accomplished, for example, by detecting spectral signatures of atomic emissions in a given material of interest. For example, the given material of interest may comprise heavy metals (such as lead, mercury, chromium, cadmium, arsenic, antimony and beryllium), alkali metals (such as lithium, potassium, rubidium, cesium and francium), radioactive materials (such as uranium, plutonium, thorium and technetium) or other materials of interest. In operation, a relatively powerful electrical spark discharge creates a small volume of hot plasma in which aerosol and solid particulates are quickly vaporized and components are reduced to atomic form. Initially, the plasma emits broadband, essentially continuous radiation. Monitoring of atomic emissions in selected wavelength bands during the relatively short period of time during which the plasma cools enables measurement of elemental concentrations.

One characteristic of current SIBS devices is that the initial plasma is created at a high temperature (e.g., from about a few thousand degrees to 10,000 degrees Celsius). These temperatures result in a high degree of ionization and subsequent recombination that creates a great deal of broadband background (Bremsstrahlung) radiation. This can be a disadvantage because it is often difficult to discriminate between the relevant spectral emissions and the broadband background emissions.

Some attempts have been made with previous laser induced breakdown spectroscopy (LIBS) devices to deal with this problem. For example, in some LIBS devices a small, fixed delay of a few to tens of microseconds is imposed between creation of the plasma and measurement of spectral emissions. While this brief, fixed delay provides some benefits, it too has various drawbacks. For example, at relatively high energies, for example 5 J or so (which is beyond the 10–250 mJ typically used in many current LIBS applications), the excitation and relaxation processes become much more complex. Some processes can be significantly delayed. As a result neither short delays nor fixed delays are optimum in all circumstances.

Other problems with traditional spark spectroscopy devices exist. For example, another type of device uses a single electrode. This single electrode spark device has various drawbacks. For example, these single electrode devices are primarily used to analyze solid, metallic samples and have limitations on their quantitative accuracy. Additionally, electrodes used in certain devices have relatively short workable lifetimes and suffer from corrosion and problems with sputtering. In some cases, the electrode itself contains material that, potentially, can interfere with the measurement of the spectral emissions of interest. Various other drawbacks exist.

One application of SIBS is as a continuously operating air pollution monitor. Existing technologies for continuous air pollution monitoring include systems based on laser excitation or employ extractive Inductively Coupled Plasma (ICP) technology. These systems are relatively expensive. A SIBS-based continuous emission monitor (CEM) does not require the expensive laser or extraction system and can be less expensive.

Another application of SIBS is as an on site monitor. Some LIBS devices have been developed for on site analysis, however, these devices are relatively expensive and suffer other drawbacks. For example, U.S. Pat. No. 5,379,103 relates to a mobile apparatus which allows in situ measurement and data collection of ground water trace element pollutants. This LIBS system is shown as having a probe coupled to a laser through a fiber optic element and another fiber optic element is used to couple the probe to spectrum analysis equipment. The spectrum is analyzed by use of an optical multichannel analyzer, a relatively costly piece of equipment. The device in the U.S. Pat. No. 5,379,103 patent appears to focus on analyzing liquid samples. These and other drawbacks exist.

SUMMARY OF THE INVENTION

An object of the present invention is to overcome these, and other problems of existing devices.

Another object of the invention is to provide a method and apparatus to efficiently and cost effectively monitor atomic emissions of predetermined materials of interest.

Another object of the invention is to provide an induced breakdown spectroscopy detection system that allows for greater control and selection of a time delay to enable improved detection of materials of interest in a plasma emission.

Another object of the invention is to provide a low cost detection system for an induced breakdown spectroscopy device that incorporates unique band pass filtering and integration times based on the materials of interest.

Another object of the invention is to provide a plasma generator for SIBS system, where the plasma generator comprises a dual electrode structure for generating a plasma.

Another aspect of the invention is the use of a dual electrode SIBS device where the electrode material is resistant to corrosion and sputtering, and which avoids using electrode materials that may interfere with measurement of the spectral lines of interest.

Another object of the invention is to provide an induced breakdown spectroscopy detection system that enables real-time, on-site monitoring, and which enables facility operators to significantly reduce worker exposure to toxic metals and reduce their operating costs.

Another object of the invention is to provide a portable, rugged, easily operated, highly reliable and sensitive on-site pollutant monitor that enables real time analysis of materials of interest.

Other objects and advantages of the invention exist.

These and other objects of the invention are accomplished by the induced breakdown spectroscopy apparatus and method described herein. According to one embodiment of the invention, a plasma generator is provided to induce a plasma. A detection system is provided to detect the emissions from the resultant plasma. A controller is provided to allow a user to select a detection time delay and an integration time. Through the controller, the user can select an optimal delay time from the induction of a plasma until spectral detection. The use of particular, predetermined, optical wavelength filters in the detection system is advantageous. Preferably, two filters of differing wavelength bands are used. The different wavelengths are chosen so that effects of background radiation can be minimized or removed from the spectral signal.

Various embodiments of this system can be used to realize one or more of the objects of the invention. For example, one embodiment relates to a SIBS system comprising a single or dual electrode, electrical spark, plasma generator. The electrode material is preferably chosen such that upon creation of plasma, the electrode does not contribute to the plasma in a way that would cause interference with the spectral emissions of interest. Preferably, the electrode material may also be resistant to corrosion and sputtering.

Various embodiments of the invention are particularly useful with relatively high power applications (e.g., on the order of 1–6 Joules). However, various aspects of the invention have broader applicability.

Other aspects of the invention will be apparent from the following discussion of the preferred embodiments.

DETAILED DESCRIPTION OF THE PREFERRED EMBODIMENTS

Figure 1:
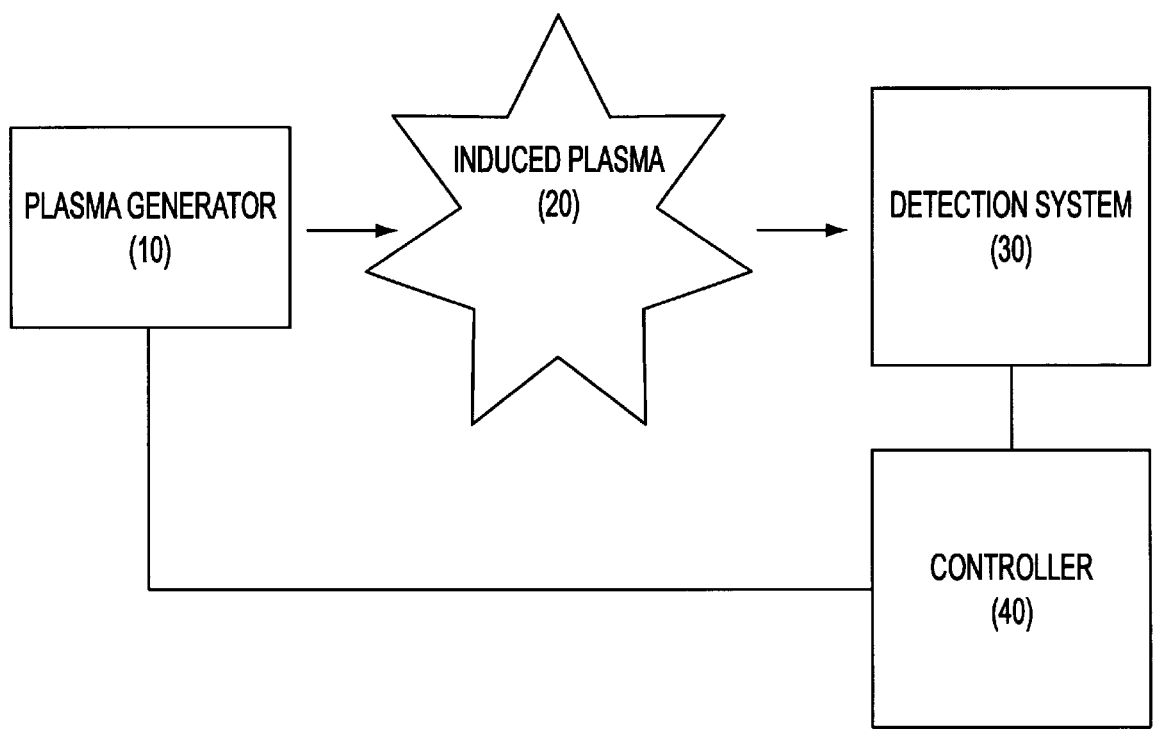
FIG. 1 is a schematic block diagram of one aspect of the present invention.

As shown in FIG. 1, one embodiment of the invention relates to, among other things, an induced breakdown spectroscopy system for measuring, for example, atomic concentrations of samples such as vapors and airborne particulates. As shown, this embodiment of the invention comprises a plasma generator 10 for inducing a plasma 20, a detection system 30 for detecting spectral signatures of atomic emissions of materials of interest in the plasma. Such materials may include, for example, heavy metals (e.g., lead, mercury, chromium, cadmium, arsenic, antimony and beryllium), radioactive materials (e.g., uranium, plutonium, thorium and technetium), or other materials of interest. A controller 40 is provided for controlling, among other things, a delay time between induction of the plasma and detection of the spectral emissions.

The plasma generator 10 is used for generating a plasma in a predetermined location that has or is suspected of having a material of interest to be detected. Almost immediately after generation of the plasma, the detector 30 is enabled by the controller 40 to detect the spectral emissions of the plasma.

A range of powers may be used to generate the plasma, depending on various relevant factors. In certain instances it may be advantageous to use a range of powers of about 1 to about 6 Joules. This relatively high range of powers compared, for example, to typical energy levels used in LIBS systems has at least two advantages. These advantages include the following. First, the higher energy release leads to a relatively larger plasma volume than LIBS: ~10 mm$^3$ for SIBS versus $\leq$0.1 mm$^3$ for LIBS. The larger volume means there are more analyte atoms to radiate, thus leading to greater sensitivity. Also, SIBS provides much better data statistics than LIBS. Most heavy metals are in particulate form, and with LIBS there is only a low probability of one or more particles being found in the breakdown volume. Thus, LIBS has to process very many pulses, many of which have no data. With SIBS, the larger volume enhances the likelihood of measuring a representative sample of particles in a single pulse.

Second, the higher energy release of SIBS, combined with the longer time delays that the present invention uses, leads to a better separation between the atomic emissions of the analyte elements and other sources of early-time radiation. Most sources of interfering radiation have high-lying energy states that decay quickly. Due to either larger volumes or higher plasma temperatures, the heavy metal emissions decay slowly and delays on the order of ~100 $\mu$s or longer can be used to get good sensitivity.

Third, SIBS provides a more effective excitation of the analyte compounds than LIBS because, the nature of the discharge is more effective at exciting analyte atoms. LIBS involves an energy deposition by light absorption. SIBS, however, deposits energy by passing an electrical current through the sample medium. The high energy electrons excite analyte atoms to many higher states compared to the energy discharge provided by light. Therefore, the more thorough, higher excitation provided by SIBS contributes to the slower decay of analyte species, enabling observation at later times and providing better separation from the emission of plasma ions and interfering compounds. When relatively high powers are used, the excitation and relaxation processes within the plasma are relatively complex. Therefore, according to one embodiment of the invention, it is desirable to enable variable delay times, to provide for integration of the detected signal and to use selected bandpass filters depending on characteristics of the material of interest.

According to one aspect of the invention, the controller 40 may be adjustable to enable predetermined delay times to be used depending on one or more of the following: the material of interest, the power level used to create the plasma, the medium where the plasma is formed and other criteria affecting the desired delay time. Preferably, a delay is imposed between the time the plasma is generated and the time the detection system is enabled for detecting the spectral emissions of the plasma. In general, the initial plasma is essentially a broadband continuum. As a result, it is difficult to accurately obtain reliable quantitative data concerning the material of interest during the time period of initial plasma radiation. This is especially true when relatively high power levels are used to generate the plasma. Shortly thereafter, the broadband radiation diminishes significantly, but the relevant spectral emissions persist. Ideally, the use of an optimal delay for a particular material of interest can enhance the reliability of the detection.

Figure 2:
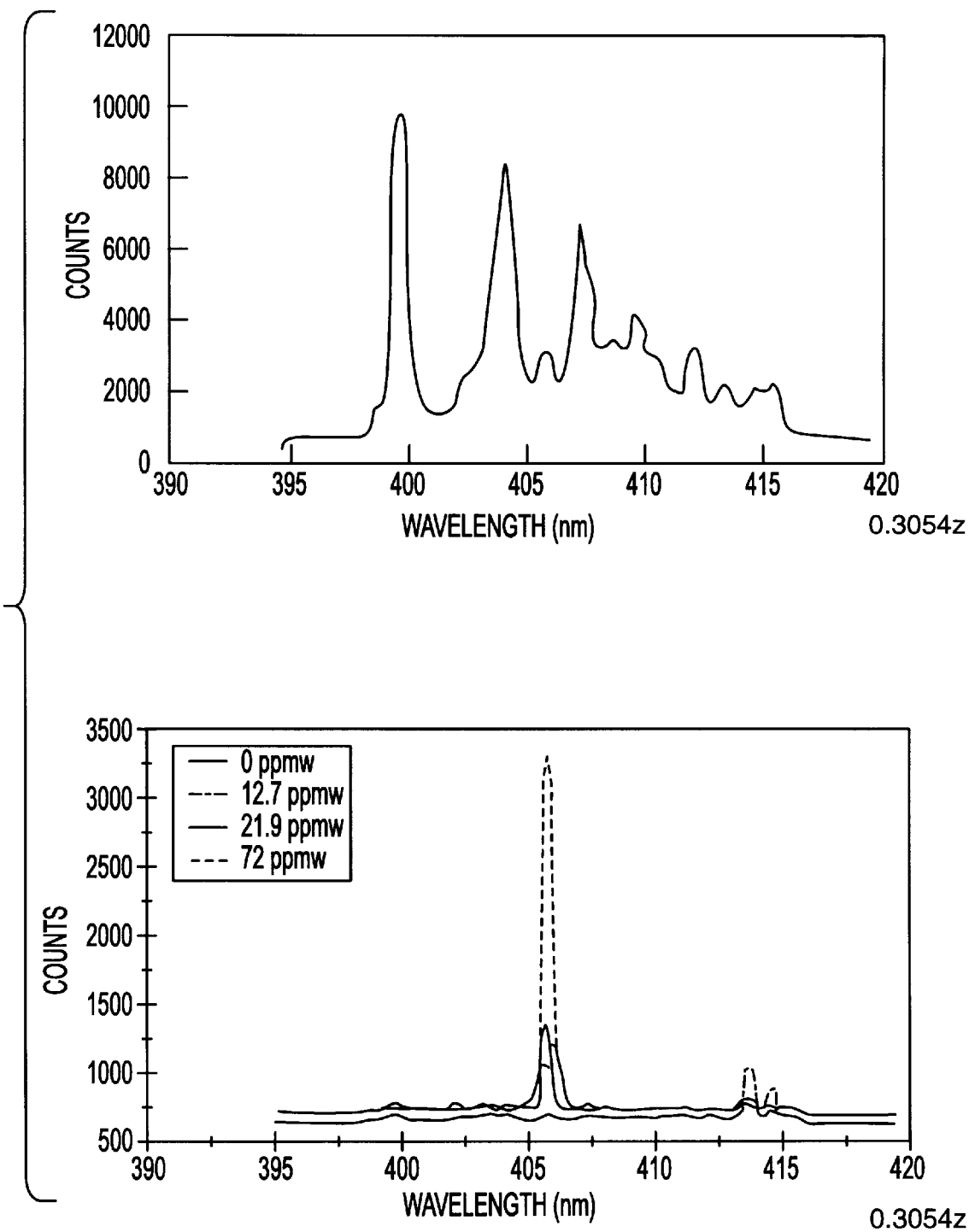
FIG. 2 shows an exemplary output of one embodiment of the invention.

For example, FIG. 2 shows the spectra of Pb at a short time (relatively no delay) and after a delay (~75 $\mu$s) with respect to a spark. The spectra is plotted as Counts vs. Wavelength (nm). The significant differences of the delayed detection with respect to the non-delayed detection are readily apparent.

Figure 3:
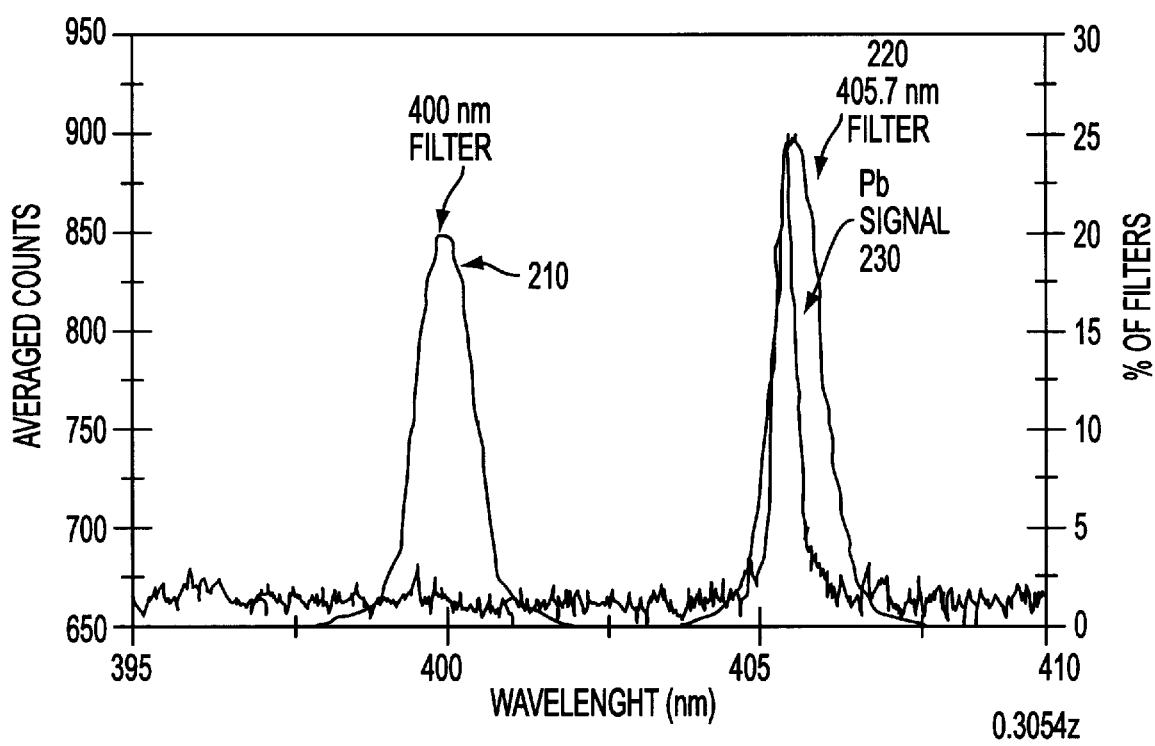
FIG. 3 shows an exemplary output of one embodiment of the invention.

Additionally, by carefully selecting an integration time and specific band pass filters, the detection reliability can be further enhanced. For example, if two bandpass filters are used in the detection system 30 it may be desirable to select a first band that does not include the spectral line(s) of interest and a second band that does include one or more of spectral line(s) of interest. The first band enables detection of background level radiation. The second band enables detection of the level of the material of interest (and background radiation within the same band). By use of various signal processing techniques, these two signals can be manipulated to improve the discrimination between the relevant spectral emissions and the broadband background emissions. For example, the background signal level from the first band may be subtracted from the signal level of the second band. Some preferred, possible combinations of filters are as follows: for Pb filters at 400 nm and 405.7 nm, for Cr filters at 420 nm and 427.5 nm. For example, for lead (Pb) the bands may be centered about an offband region (e.g., 400 nm) and centered on a Pb atomic transition line (e.g., 405.7 nm), respectively. The bands can have any reasonable width consistent with the resulting trade-off. For example, the bands should be relatively narrow to reduce noise and interference. As illustrated in FIG. 3, the peak due to the 400 nm filter is shown as reference number 210, the peak due to the 405.7 nm filter is shown as reference number 220 and the peak due to the Pb emission is shown as reference number 230. In general, the selection of the desirable bands for the off band filter involves consideration of substantially avoiding spectral lines of elements likely to be in the matrix, including electrode material. The second band filter is preferably substantially centered on a transition associated with an expected emission peak for a material of interest.

Additionally, the signals may be integrated over a period of time. This may be done by summing the intensity of the emissions that occur during a selected time interval. Generally, the integration time is selected based on the duration of the intensity of the atomic emission of the material of interest and is selected to maximize separation between atomic emission and early plasma broad-band emission.

If desired, the system may include a display device to enable the user to observe and select the delay and integration time periods. The display device shows the raw data traces from the two filtered channels (e.g., for Pb: 400 nm and 405.7 nm), the difference between the two channels and the integrated difference that is directly proportional to the concentration of the material of interest. The concentration can be displayed as a strip chart recording and provides a real time record of the material of interest's concentration. For example, one embodiment uses a controller based upon a fast digital to analog data acquisition board (e.g., a 1.2 Mega-samples/sec (MS/s) board). The board allows the controller to acquire and process data from two filter channels of the detection system. This allows time resolutions of 2 $\mu$s per channel, signal averaging and processing. By controlling one or more of the delay time, integration time and band pass filter combinations, improved readings can be obtained.

At least three advantages result from the above controller and detection system. First, the user is provided with real time displays, including displays of the temporal evolution of the plasma emissions. This allows the user to optimize at least one of the delay time and integration time to obtain the maximum sensitivity to the material of interest. Second, the data can be written to a file. This allows more sophisticated data analysis (e.g., spread sheets, regressions, etc.) to be performed at the completion of the data acquisition. Third, because signal averaging can be used, the precision and reliability of the measured concentration of the material of interest is improved.

Figure 4:
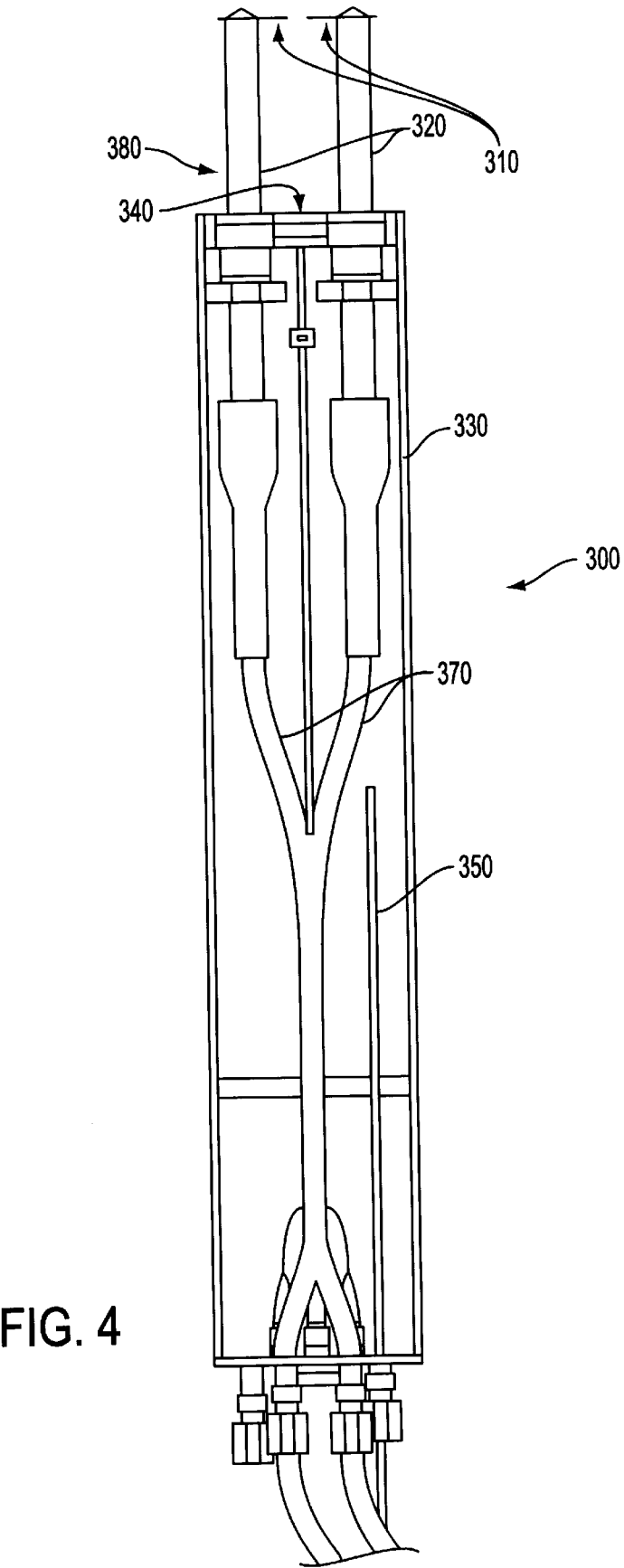
FIG. 4 shows a portion of a SIBS embodiment of the invention.

While these features may be carried out by various structural configurations, a preferred embodiment uses a SIBS type plasma generator with a dual electrode structure. An example of the major structural components of one embodiment of a SIBS detector according to this aspect of the invention is shown in FIG. 4. As shown, the system of this embodiment comprises a dual electrode SIBS probe 300. The probe 300 comprises a housing 330 that can be any convenient size and shape. As shown, the housing is generally cylindrical. The system further comprises an electrode assembly 380. The electrode assembly 380 comprises electrodes for generating an electric spark discharge to enable the creation of a plasma. Preferably, the electrode assembly comprises two electrodes 310. At least a portion of the electrode assembly 380 is external to the housing 330. Preferably, a portion of the electrode assembly 380 is located within the housing 330 and is mounted in a suitable manner. For example, the two electrodes 310 are shown mounted on insulating standoffs 320. The standoffs are coupled with housing 330 in a suitable manner for example, by feed throughs. The electrode assembly 380 may be preferably connected to a suitable source of power to enable the generation of a plasma. Connection may be made in any suitable manner. For example, two electric conductors 370 are shown, each of which connects one electrode 310 of electrode assembly 380 to a suitable power source (not shown). The system preferably further comprises a mechanism for enabling coupling of light emitted by the plasma into the detection system, for example, one or more fiber optic elements 340. The fiber optic elements 340 are preferably located at a suitable position to enable the coupling of light emitted by the plasma into the detection system 30. For example, fiber optic elements 340 may located near standoffs 320. Suitable lenses and other coupling elements may be used. The fiber feeds the respective filters and the triggering device. A thermocouple element 350 (or other suitable device) may be used in some embodiments to monitor the temperature inside the housing 330.

According to another aspect of the invention the electrodes 310 of the SIBS-based plasma generator comprise specific materials chosen to improve the reliability of the detection. For example, during the plasma generation, it is possible for atoms of the electrode to be vaporized along with the material of interest. To avoid this and other problems, the electrodes 310 comprise materials that will minimize or reduce interference with the detection. Because of the high temperatures involved, the electrodes of a SIBS system should be resistant to corrosion and sputtering. Electrodes that have relatively high melting points are consistent with these objectives. For example, preferable electrode materials Re, Ir, Rh and Ta have melting points of 3180° C., 2410° C., 1966° C., and 2966° C., respectively. Transition metals such as Re, Ir, Rh and Ta also do not interfere with the spectra of, for example, the heavy metals and radioactive elements, and also provide good corrosion and sputtering resistance.

By way of example, a SIBS embodiment may operate as follows:

According to one aspect of the invention, a method for analysis of airborne species uses a pulsed spark and variable delay detection. The SIBS spark is formed using a pair of special electrodes 310. The spark is generated by a plasma generator comprising a power supply (not shown) connected to electrode assembly 380 through connections 370. The plasma generator provides the energy for the discharge and, with the controller, a method of synchronizing the discharge with external signal processing and timing electronics. This circuit initially generates pre-ignition sparks that are characterized by relatively short (e.g., ~1–10 $\mu$s), low-energy (e.g., <0.1 J), high-voltage (e.g., >40 kV) sparks across the electrodes (not un-like those produced by the spark plugs of an automobile engine), these pre-ignition sparks provide a conduction path for a primary capacitor (not shown), which is kept charged by a second power supply (not shown). Almost immediately after the high voltage spark is struck, the primary capacitor discharges, providing the majority of the pulse energy. The pulsed spark ionizes the air volume between and around the electrodes. This hot plasma may also vaporize particles that contain the material(s) of interest. The vaporized materials of interest and any gaseous materials are excited into higher energy states. After a short period of time the plasma cools while the emission from the materials of interest persists. This allows sensitive optical detection of the emissions from the materials of interest.

This in-situ technique has several advantages over other methods such as LIBS in that the SIBS spark can be generated using a simple electrical circuit and does not need a laser source. In addition, the energy contained in the SIBS spark can be several joules (preferably, from about 0.3 to about 6 J) and relatively large volumes of air (approximately 10 mm$^3$) can be examined in each pulse.

The plasma may be induced by laser, spark or in another suitable manner. The detector may comprise a photomultiplier tube (PMT) or other suitable radiant energy detector. The emitted light from the plasma may be coupled into the detector with fiber optics or other suitable mechanism. Preferably, the detector is operatively connected through a controller to the plasma generator to synchronize the timing of the detection period. In this manner, the time delay selected by the user can be precisely clocked to run from the point of plasma generation.

The invention may be incorporated into many applications. For example, one application may comprise use as pollution monitoring devices. Detecting and monitoring particulate pollution is a major concern for many industries and agencies. For example, airborne lead particles represent a serious threat to workers in the approximately 7,000 gun firing ranges in the United States. There are also several thousand smelting and metal processing plants with occupational health concerns involving airborne heavy metals.

A portable embodiment may be used by environmental engineering firms for on-site, real-time detection of materials of interest.

Another application comprises real time analysis and output for process control, such as removal of lead paint.

Other embodiments and uses of the invention will be apparent to those skilled in the art from consideration of the specification and practice of the invention disclosed herein. The specification and examples should be considered exemplary only. The intended scope of the invention is only limited by the claims appended hereto.

What is claimed is:

1. An induced breakdown spectroscopy system with controllable delay time for detecting a material of interest, the system comprising:
    generating means, located near said material of interest, for generating a high energy pulse to create a plasma;
    detector means for detecting and measuring a material of interest in the plasma based on spectral emissions of the material of interest;
    a processor connected to an output of the detector means, said processor comprising: filter means to filter out undesirable spectral regions from the detector signal;
    wherein said filter means comprise one or more bandpass filters; and
    wherein at least one of said one or more bandpass filters is substantially centered to pass spectral emissions that contain at least part of the spectral emissions of said material of interest;
    delay means for causing a controllable delay between the time of generation of the plasma and the time of detecting and measuring; and
    user control means for controlling the duration of said delay.

2. The system of claim 1 wherein the generating means comprises a spark generating means.

3. The system of claim 1 wherein the high energy pulse is in the range of approximately 0.3–6 Joules.

4. The system of claim 1 wherein the generating means comprises a pair of electrodes for creating the plasma.

5. The system of claim 1 wherein the generating means comprises at least one electrode, and the at least one electrode comprises a material chosen to reduce interference with the detection and measuring.

6. The system of claim 1 wherein the generating means comprises at least one electrode, and the at least one electrode comprises a material chosen to be resistant to corrosion.

7. The system of claim 1 wherein the generating means comprises at least one electrode, and the at least one electrode comprises a material chosen to be resistant to sputtering.

8. The system of claim 1 wherein the generating means comprises at least one electrode, and the at least one electrode comprises a material chosen to be resistant to corrosion and sputtering.

9. The system of claim 1 wherein the generating means comprises at least one electrode, and the at least one electrode comprises a material chosen to have a sufficiently high melting point to reduce degradation and sputtering of the at least one electrode.

10. The system of claim 1 wherein the generating means comprises at least one electrode, and the at least one electrode comprises a material chosen have a melting point of about 1900° C. or higher.

11. The system of claim 1 wherein the generating means comprises at least one electrode, and the at least one electrode comprises a material chosen from the group consisting of Re, Ir, Rh and Ta.

12. The system of claim 1 wherein the delay is chosen based at least on the energy level of the pulse generated by the generating means.

13. The system of claim 1 wherein the plasma initially comprises broadband radiation, and the delay is chosen to cause a delay in the detection that is long enough for the broadband radiation to diminish but not longer than the time period for which the spectral emissions of the material of interest persist.

14. The system of claim 13 wherein the generating means comprises at least one electrode, and the at least one electrode comprises a material chosen to be resistant to corrosion.

15. The system of claim 13 wherein the generating means comprises at least one electrode, and the at least one electrode comprises a material chosen to be resistant to sputtering.

16. The system of claim 13 wherein the generating means comprises at least one electrode, and the at least one electrode comprises a material chosen to be resistant to corrosion and sputtering.

17. The system of claim 13 wherein the generating means comprises at least one electrode, and the at least one electrode comprises a material chosen to have a sufficiently high melting point to reduce degradation and sputtering of the at least one electrode.

18. The system of claim 13 wherein the generating means comprises at least one electrode, and the at least one electrode comprises a material chosen have a melting point of about 1900° C. or higher.

19. The system of claim 13 wherein the generating means comprises at least one electrode, and the at least one electrode comprises a material chosen from the group consisting of Re, Ir, Rh and Ta.

20. The system of claim 1 wherein said processor further comprises integrator means for integrating the detector signal over a variable time period.

21. The system of claim 20 wherein the variable time period of said integrator means is user controllable.

22. The system of claim 1 wherein at least one of said one or more bandpass filters is substantially centered to pass spectral emissions that do not contain the spectral emissions of said material of interest.

23. An induced breakdown spectroscopy system with a user controllable delay time for detecting a material of interest, the system comprising:

means for generating a high energy pulse to create a plasma, said generating means located near said material of interest;

means for detecting and measuring a material of interest in said plasma based on spectral emissions of the material of interest;

means for causing a controllable delay between a time of generation of said plasma and a time of detecting and measuring;

means for controlling a duration of said user controllable delay; and a processor connected to an output of the detector means, said processor comprising:

one or more bandpass filters to filter out undesirable spectral regions from the detector signal, at least one of said one or more bandpass filters is substantially centered to pass spectral emissions that contain at least part of the spectral emissions of said material of interest.

24. The system of claim 23 wherein said generating means comprises at least one electrode, and the at least one electrode comprises a material chosen to be resistant to corrosion.

25. The system of claim 23 wherein said generating means comprises at least one electrode, and the at least one electrode comprises a material chosen to be resistant to sputtering.

26. The system of claim 23 wherein said generating means comprises at least one electrode, and the at least one electrode comprises a material chosen to be resistant to corrosion and sputtering.

27. The system of claim 23 wherein said generating means comprises at least one electrode, and the at least one electrode comprises a material chosen to have a sufficiently high melting point to reduce degradation and sputtering of the at least one electrode.

28. The system of claim 23 wherein said generating means comprises at least one electrode, and the at least one electrode comprises a material chosen have a melting point of about 1900° C. or higher.

29. The system of claim 23 wherein said generating means comprises at least one electrode, and the at least one electrode comprises a material chosen from the group consisting of Re, Ir, Rh and Ta.

30. The system of claim 23 wherein at least one of said one or more bandpass filters is substantially centered to pass spectral emissions that do not contain the spectral emissions of said material of interest.

* * * * *

UNITED STATES PATENT AND TRADEMARK OFFICE
CERTIFICATE OF CORRECTION

| | | |
|---|---|---|
| PATENT NO. | : 6,034,768 | Page 1 of 1 |
| APPLICATION NO. | : 09/114147 | |
| DATED | : March 7, 2000 | |
| INVENTOR(S) | : Fraser et al. | |

It is certified that error appears in the above-identified patent and that said Letters Patent is hereby corrected as shown below:

At column 1, line 7, before the section entitled "FIELD OF THE INVENTION," please insert the following section:

-- GOVERNMENT RIGHTS

The invention was made with government support from the U.S. Navy under grant no. N47408-C-7320. The government may have certain rights in the invention --

Signed and Sealed this
First Day of February, 2011

David J. Kappos
*Director of the United States Patent and Trademark Office*